United States Patent [19]

Bisacchi et al.

[11] Patent Number: 4,588,828
[45] Date of Patent: May 13, 1986

[54] ACETYLENIC ANTIBIOTICS

[75] Inventors: Gregory S. Bisacchi, Neshanic; William H. Koster, East Amwell Township, Macomb County, both of N.J.

[73] Assignee: E. R. Squibb & Sons, Inc., Princeton, N.J.

[21] Appl. No.: 643,592

[22] Filed: Aug. 23, 1984

[51] Int. Cl.$^4$ .................. C07D 303/32; C07D 303/14
[52] U.S. Cl. .................... 549/548; 549/560; 549/554; 549/555; 549/416; 568/873
[58] Field of Search ............... 549/548, 554, 555, 560

[56] References Cited

PUBLICATIONS

Parker et al, Journal of Antibiotics, vol. XXXVII, No. 5, pp. 431–440 (1984).
Jones et al., Journal of the Chemical Society, pp. 2048–2055, (1963).
Bohlmann et al., Chemische Berichte, vol. 95, pp. 1742–1747, (1962).
Eisner et al., Journal of the American Chemical Society, 1372–1379 (1953).

Primary Examiner—Norma S. Milestone
Attorney, Agent, or Firm—Lawrence S. Levinson; Donald J. Barrack

[57] ABSTRACT

Antimicrobial activity is exhibited by compounds having the formula

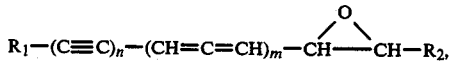

wherein
$R_1$ is hydrogen or aryl;
$R_2$ is hydroxymethyl, carboxyaldehyde, propenalyl, 3-hydroxy-1-propenyl, or 3-hydroxy-1,2-epoxypropyl; and
n is 2 and m is 1 or n is 3 and m is 0; with the proviso that if $R_1$ is hydrogen, n is 2 and m is 1.

12 Claims, No Drawings

ACETYLENIC ANTIBIOTICS

BACKGROUND OF THE INVENTION

The Journal of Antibiotics, Vol. XXXVII No. 5, page 431 (1984), discloses cepacin, a natural product found to be made up of two compounds; i.e., 5-[3-[3-(hepta-1,2-dien-4,6-diynyl)oriran-2-yl]-3-hydroxy-1-propenyl]-dihydro-2(3H)-furanone, a compound of the formula

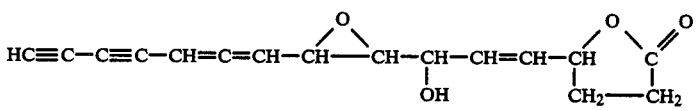

referred to as cepacin A, and 5-[[3-[3-(hepta-1,2-dien-4,6-diynyl)-2-oxiranyl]-2-oxiranyl]hydroxymethyl]-dihydro-2(3H)-furanone, a compound having the formula

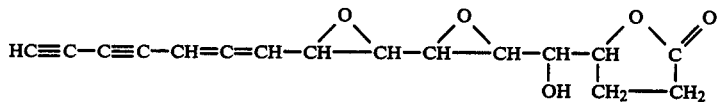

referred to as cepacin B.

Journal of the Chemical Society, 2048 (1963) discloses an acetylenic epoxy alcohol having the formula

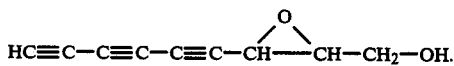

Chemische Berichte, 95, 1742 (1962) discloses an acetylenic compound having the formula

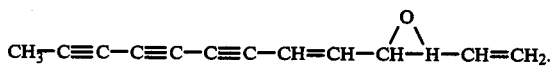

Journal of the American Chemical Society 1372 (1953), discloses a diacetylenic tetraolefinic compound having the formula

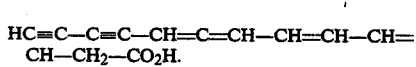

SUMMARY OF THE INVENTION

Compounds having the formula

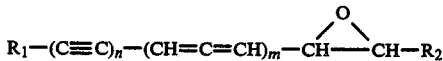

have antimicrobial activity. In formula I, and throughout the specification, the symbols are as defined below.

$R_1$ is hydrogen or aryl;

$R_2$ is hydroxymethyl, carboxyaldehyde, propenalyl, 3-hydroxy-1-propenyl, or 3-hydroxy-1,2-epoxypropyl; and n is 2 and m is 1 or n is 3 and m is 0; with the proviso that if $R_1$ is hydrogen, n is 2 and m is 1.

The term "aryl", as used throughout the specification, refers to phenyl and phenyl substituted with 1, 2 or 3 halogen, alkyl (of 1 to 4 carbons), alkoxy (of 1 to 4 carbons) or trifluoromethyl groups.

DETAILED DESCRIPTION OF THE INVENTION

The compounds of formula I wherein n is 3 and m is 0 can be prepared by first coupling an aryl diacetylene having the formula

wherein $R'_1$ is aryl, with a 1-bromo substituted acetylene having the formula

The coupling is carried out in the presence of a copper catalyst, e.g., cuprous chloride, and yields the corresponding compound having the formula

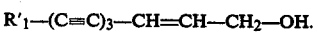

Oxidation of a compound of formula IV using a vanadium catalyst and an oxidizing agent such as t-butyl hydroperoxide yields a product of this invention having the formula

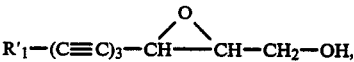

as a racemic mixture. To get an enantiomerically pure product, tetraisopropoxy titanium and (+)− or (−)-dimethyl tartrate, and t-butyl hydroperoxide can be used when oxidizing a compound of formula IV. The use of (+)-dimethyl tartrate yields one enantiomer of the compound of formula V and the use of (−)-dimethyl tartrate yields the other enantiomer of the compound of formula V.

Oxidation of a compound of formula V using, for example, chromium trioxide, yields the corresponding product of this invention having the formula

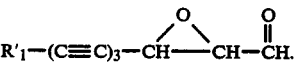

Treatment of a compound of formula VI with a Wittig agent yields the corresponding product of this invention having the formula

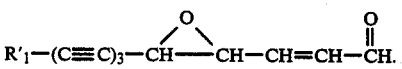

Reduction of a compound of formula VII with a reducing agent such as diisobutylaluminum hydride yields the corresponding product of this invention having the formula

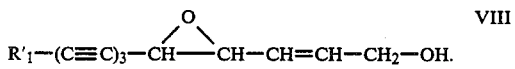

Oxidation of a compound of formula VIII using a vanadium catalyst and an oxidizing agent such as t-butyl hydroperoxide yields the corresponding product of this invention having the formula

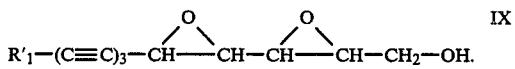

Oxidation can also be accomplished using tetraisopropoxy titanium, (+)- or (−)-dimethyl tartrate, and t-butyl hydroperoxide. The stereochemistry of a compound of formula IX will depend on the stereo-chemistry of the starting compound of formula VIII (racemic or enantiomerically pure) and on the reactants used for the oxidation. The compound of formula IX can be a mixture of diastereomers or a single diastereomer. These diastereomers can be racemic or enantiomerically pure.

The compounds of formula I wherein n is 2 and m is 1 can be prepared by first initiating a palladium-mediated coupling between a zinc acetylide having the formula

and a monosubstituted acetylene having the formula

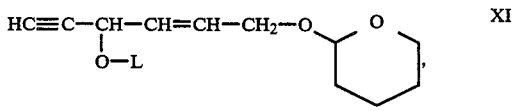

wherein "OL" is a leaving group such as acetate, tosylate, mesylate or the like, to obtain the corresponding compound having the formula

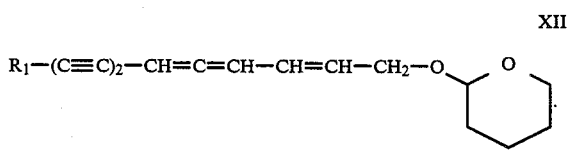

Conversion of a compound of formula XII to the corresponding product of this invention wherein $R_2$ is hydroxymethyl can be accomplished by treating a compound of formula XII with methanol (or other deprotecting conditions) to obtain the corresponding compound having the formula

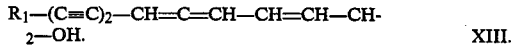

Conversion of a compound of formula XIII to the corresponding products of this invention wherein $R_2$ is carboxyaldehyde, propenalyl, 3-hydroxy-1-propenyl, and 3-hydroxy-1,2epoxypropyl, can be accomplished using the sequential methodology described above for the conversion of a compound of formula IV to the corresponding products of formula I.

The compounds of this invention each contain at least one asymmetric carbon atom and accordingly exist in stereoisomeric forms or racemic mixtures thereof. The preparation of a mixture of diastereomers or a single diastereomer, said diastereomers being racemic or enantiomerically pure has been described above. All are contemplated as part of this invention.

The compounds of this invention have activity against a range of gram-negative and gram-positive organisms and can be used as agents to combat bacterial infections (including urinary tract infections and respiratory infections) in mammalian species, such as domesticated animals (e.g., dogs, cats, cows, horses, and the like) and humans.

For combating bacterial infections in mammals, a compound of this invention can be administered to a mammal in need thereof in an amount of about 1.4 mg/kg/day to about 350 mg/kg/day, preferably about 14 mg/kg/day to about 100 mg/kg/day. All modes of administration which have been used in the past to deliver penicillins and cephalosporins to the site of the infection are also contemplated for use with the compounds of this invention. Such methods of administration include oral, intravenous, intramuscular, and as a suppository.

The following examples are specific embodiments of this invention.

EXAMPLE 1

(trans)-3-(7-Phenyl-1,2-heptadiene-4,6-diynyl)-oxiranemethanol (A) trans-2-Butene-1,4-diol, monotetrahydropyranyl ether To a solution of trans-2-butene-1,4-diol (7.57 g, 85.9 mmole) and a catalytic quantity of p-toluenesulfonic acid in 700 ml of dry ether was added dihydropyran (6.73 ml, 71.6 mmole) at the rate of 1.5 ml/hour. After stirring for four days, the reaction mixture was washed with saturated sodium bicarbonate, and the organic layer was separated and dried over sodium sulfate and concentrated in vacuo to afford the crude product which was purified via flash chromatography (LPS-1 silica gel; ether-hexane 1:1) to provide the title compound (5.75 g).

(B) 4-Hydroxy-2-butenal, tetrahydropyranyl ether trans-2-Butene-1,4-diol, monotetrahydropyranyl ether (5.57 g, 33.4 mmole) and 42 g (0.48 mole) of activated manganese dioxide were stirred in 300 ml of dry methylene chloride under nitrogen for 24 hours. The reaction mixture was filtered through Celite, washed copiously with methylene chloride and concentrated in vacuo. The crude product was purified via flash chromatography (LPS-1 silica gel; ether-hexane 1:1) to afford 1.83 g of the title compound along with 1.75 g of recovered starting material.

(C) 6-[(Tetrahydro-2H-pyran-2-yl)oxy]-4-hexen-1-yn-3-ol

A stirred, saturated solution of acetylene in 22 ml of dry tetrahydrofuran at −78° C. was treated dropwise with n-butyllithium (11.9 mmole). After stirring 10 minutes at −78° C., 4-hydroxy-2-butenal, tetrahydropyranyl ether (1.83 g, 10.8 mmole) in 3 ml of dry tetrahydrofuran was added dropwise. After stirring at −78° C., the reaction mixture was warmed to room temperature. Water (4 ml) was added followed by anhydrous potassium carbonate until the aqueous phase became pasty. The organic phase was decanted and the aqueous layer was washed with ether. The combined organic phase was dried over magnesium sulfate and concentrated in vacuo. Flash chromatography of the crude product (LPS-1 silica gel; ethyl acetate-hexane 1:1) afforded the title compound which was distilled (bulb-to-bulb) to provide pure material (1.55 g).

(D) 10-Phenyl-deca-7,9-diyne-2,4,5-trien-1-ol, tetrahydropyranyl ether n-Butyllithium (1.5 mmole) was added dropwise to a stirred −78° C. solution of phenyl-diacetylene (189 mg, 1.5 mmole) in 15 ml of dry tetrahydrofuran. The mixture was stirred for one-half hour at −78° C. and then warmed to −20° C. whereupon a solution of anhydrous zinc chloride in tetrahydrofuran (2.1 ml of a 0.78 M solution; 1.5 mmole) was added dropwise. After addition was complete, the mixture was stirred at −20° C. for one-half hour whereupon a catalytic amount of tetrakis (triphenylphosphine) palladium (O) was added (30 mg dissolved in 1 ml of tetrahydrofuran). The mixture was stirred for one-half hour at −20° C.

In a separate flask, the mesylate of 6-[(tetrahydro-2H-pyran-2-yl)oxy]-4-hexen-1-yn-3-ol was prepared via the following procedure. To a stirred solution of 6-[(tetrahydro-2H-pyran-2-yl)oxy]-4-hexen-1-yn-3-ol (294 mg, 1.5 mmole), anhydrous lithium bromide (130 mg, 1.5 mmole), and a few milligrams of 1,10-phenanthroline in 7 ml of tetrahydrofuran at −78° C. was added n-butyllithium dropwise until a brown solution was obtained (ca. 1.5 mmole of n-butyllithium). The mixture was stirred for one-half hour at −78° C. whereupon mesyl chloride (114 μl, 171 mg, 1.5 mmole) was added dropwise. The brown color discharged to yellow. The solution was stirred for one-half hour at −78° C. and was then added all at once (via a short Teflon cannula and argon pressure) to the above stirred −20° C. solution of zinc phenyldiacetylene. The resultant mixture was stirred at −20° C. for 15 minutes and was then acidified by the addition of a solution of acetic acid in tetrahydrofuran. This mixture was then concentrated to ca. ¼ volume and 30 ml of a mixture of ether-hexane 1:1 was added with stirring whereupon a gum separated. The supernatant was then filtered through a pad of silica gel. The filtrate was then concentrated to dryness and immediately redissolved in a few ml of ether-hexane 1:5 (some solid does not dissolve). This solution of crude product was then purified via flash chromatography (LPS-silica gel, ether-hexane 1:10) to afford the title compound (90 mg). This allene must be stored in a non-basic, non-hydroxylic solvent in the freezer.

(E) 10-Phenyl-7,9-decadiyne-2,4,5-trien-1-ol

To a stirred solution 40 mg of 10-phenyldeca-7,9-diyne-2,4,5-trien-1-ol, tetrahydropyranyl ether in tetrahydrofuran-acetonitrile 1:3 was added one drop of 15% aqueous hydrochloric acid. The mixture was stirred at room temperature for four hours. Most of the solvent was then removed in vacuo and the residue was taken up in ether. The ethereal solution was washed three times with water, once with brine and dried over sodium sulfate. The crude product was flash chromatographed (LPS-1 silica gel, ether-hexane 1:7) to afford 8 mg of the title compound plus 16 mg of recovered starting material.

(F) (trans)-3-(7-Phenyl-1,2-heptadiene-4,6-diynyl)oxiranemethanol

To a stirred solution of 20 mg (0.090 mmole) of 10-phenyl-7,9-decadiyne-2,4,5-trien-1-ol in 4 ml of benzene was added 2 mg of vanadyl acetylacetonate and 50 μl (0.26 mmole) of a 5.43M solution of t-butyl hydroperoxide in benzene. The mixture was stirred for two hours. The mixture was concentrated and the residue was purified via flash chromatography to afford 7 mg of the title compound as an approximately 1:1 mixture of diastereomers.

EXAMPLE 2

(trans)-3-(1,2-Heptadiene-4,6-diynyl)oxiranemethanol (2 isomers)

(A) 2,4,5-Decatriene-7,9-diyn-1-ol, tetrahydropyranyl ether n-Butyllithium (0.5 mmole) was added slowly dropwise to a stirred −78° C. solution of diacetylene (1.0 mmole) in 15 ml of dry tetrahydrofuran. The mixture was stirred for one-half hour at −78° C. and then warmed to −20° C. whereupon a solution of anhydrous zinc chloride in tetrahydrofuran (0.5 mmole; 0.68 ml of a 0.73 M solution) was added rapidly dropwise. After addition was complete, the mixture was stirred at −20° C. for one-half hour whereupon a catalytic amount of tetrakis(triphenylphosphine)palladium (O) was added (20 mg dissolved in 1 ml tetrahydrofuran). The mixture was stirred for one-half hour at −20° C.

In a separate flask, the mesylate of 6-[(tetrahydro-2H-pyran-2-yl)oxy]-4-hexen-1-yn-3-ol was prepared via the following procedure. To a stirred solution of 6-(tetrahydro-2H-pyran-2-yl)oxy]-4-hexen-1-yn-3-ol (98 mg, 0.5 mmole), anhydrous lithium bromide (43 mg, 0.5 mmole) and a few milligrams of 1,10-phenanthroline in 5 ml of tetrahydrofuran at −78° C. was added n-butyllithium dropwise until a brown color was obtained (ca. 0.5 mmole of n-butyllithium). The mixture was stirred for one-half hour whereupon mesyl chloride (38 μl, 0.5 mmole) was added dropwise. The brown color discharged to yellow. The solution was stirred for 10 minutes at −78° C. and was then added all at once (via short teflon cannula and argon pressure) to the above stirred −20° C. solution of zinc diacetylene. The resultant mixture was stirred at −20° C. for 15 minutes and was then acidified by the addition of a solution of acetic acid in tetrahydrofuran. The mixture was then concentrated to ca. ¼ volume and 30 ml of a mixture of ether-hexane 1:1 was added with stirring whereupon a gum separated. The supernatant was then filtered through a pad of silica gel. The filtrate was concentrated to dryness and immediately redissolved in a few ml of ether-hexane 1:5 (some solid did not dissolve). This solution of crude product was then purified via flash chromatography (LPS-1 silica gel, ether-hexane 1:10) to afford pure title compound (30 mg). This allene was stored in solution in ether-hexane in the freezer.

(B) 2,4,5-Decatriene-7,9-diyn-1-ol

A solution of 95 mg (0.42 mmole) of 2,4,5-decatriene-7,9-diyn-1-ol, tetrahydropyranyl ether was stirred in 37 ml of reagent methanol for 2 hours at room temperature. The solvent was removed in vacuo and the residue immediately redissolved in ca. 1 ml of ether-hexane 1:3. This solution of crude product was then purified by flash chromatography (LPS-1 silica gel, ether-hexane 1:5) to afford 41 mg of the title compound which was stored in ether-hexane solution in the freezer.

(C)

(trans)-3-(1,2-Heptadiene-4,6-diynyl)oxiranemethanol

To a stirred solution of 39 mg (0.27 mmole) of 2,4,5-decatriene-7,9-diyn-1-ol in 7 ml of dry benzene was added 10 mg of vanadyl acetylacetonate and 200 μl (1.09 mmole) of a 5.43M solution of t-butyl hydroperoxide in benzene. The mixture was stirred for 3 hours at room temperature. The mixture was concentrated to a small volume (ca. 1.5 ml) and purified via flash chromatography (LPS-1 silica gel, ether-hexane 1:5) to afford 5.3 mg of one epoxide diastereomer of the title compound (Rf 0.24, ethyl acetate-hexane 1:3) and 8.0 mg of the second epoxide diastereomer of the title compound (Rf 0.20, ethyl acetate-hexane 1:3).

EXAMPLE 3

(trans)-3-(6-Phenyl-1,3,5-hexatriynyl)oxiranemethanol (A) (E)-9-Phenyl-2-nonene-4,6,8-triyn-1-ol Freshly prepared phenyldiacetylene (4.0 g, 31.7 mmole) was dissolved in 45 ml of oxygen-free methanol, cooled to 0° C. Cuprous chloride (90 mg) and hydroxylamine hydrochloride (300 mg) were dissolved in 40 ml of oxygen-free 70% aqueous ethylamine, and the resulting solution was then added in one portion to the above stirred solution of phenyldiacetylene. To this mixture was then added dropwise a solution of 6.64 g (41.3 mmole) of 5-bromopent-2-en-4-yn-1-ol in 45 ml of oxygen-free tetrahydrofuran. This mixture was stirred for 45 minutes at 0° C. Water was added and the mixture was extracted with ether. The combined ether extracts were washed with water, brine, and dried over anhydrous magnesium sulfate. Removal of solvent and flash chromatography of the residue on LPS-1 silica gel (ether-hexane, 1:1) afforded 3.15 g of the title compound.

(B)

(trans)-3-(6-Phenyl-1,3,5-hexatriynyl)oxiranemethanol

To a stirred solution of 103 mg (0.50 mmole) of (E)-9-phenyl-2-nonen-4,6,8-triyn-1-ol in 20 ml of dry benzene was added 5 mg of vanadyl acetylacetonate and 0.095 ml (0.50 mmole) of a 5.24M solution of t-butylhydroperoxide in benzene. Further 0.095 ml potions of t-butyl hydroperoxide solution were added after 2 hours and 3½ hours. After stirring for 18 hours, the benzene solution was concentrated and purified via preparative thin layer chromatography (Analtech, 2 mm, silica gel; ether-hexane 1:1) to afford 59 mg of the title compound, melting point 68°-70° C.

Analysis Calc'd. for $C_{15}H_{10}O_2$: C, 81.07; H, 4.54. Found: C, 80.34; H, 4.52.

EXAMPLE 4

(trans)-3-(6-Phenyl-1,3,5-hexatriynyl)oxiranecarboxaldehyde

Chromium trioxide (951 mg, 9.51 mmole; dried in vacuo over phosphorous pentoxide) was added to a stirred solution of 1.49 g (18.88 mmole) of dry pyridine in 25 ml of dry methylene chloride. The deep red solution was stirred for 15 minutes at room temperature. A solution of (trans)-3-(6-phenyl-1,3,5-hexatriynyl)oxiranemethanol (300 mg, 1.35 mmole; see Example 3) in 5 ml of dry methylene chloride was then added in one portion. A tarry, black deposit separated immediately. After stirring for 20 minutes at room temperature, the solution was decanted and filtered through a pad of silica gel. Several portions of ether were then passed through the silica gel. Solvent was removed from the combined filtrates and the residue was chromatographed on silica gel (ether-hexane) to afford 130 mg of the title compound.

EXAMPLE 5

(trans)-3-[3-(6-Phenyl-1,3,5-hexatriynyl)oxiranyl]-2-propenal (trans)-3-(6-Phenyl-1,3,5-hexatriynyl)oxiranecarboxaldehyde (80 mg, 0.36 mmole; see Example 4) and formylmethylenetriphenylphosphorane (122 mg, 0.40 mmole) were dissolved in 10 ml of dry benzene and the mixture was heated at 70° C. for 10 minutes. The mixture was then cooled to room temperature and the solvent was removed in vacuo. The residue was taken up in ether and filtered through a plug of silica gel. Removal of solvent afforded a brown oil which was purified by chromatography (silica gel, ether-hexane 1:1) to afford 46 mg of the title compound, melting point 91°-92.5° C.

Analysis Calc'd. for $C_{17}H_{10}O_2$: C, 82.91; H, 4.09. Found: C, 82.92; H, 4.19.

EXAMPLE 6

(trans)-3-[3-(6-Phenyl-1,3,5-hexatriynyl)oxiranyl]-2-propen-1-ol

Diisobutylaluminum hydride (0.35 ml of a 1.76 M solution in toluene, 0.61 mmole) was added dropwise to a stirred −78° C. solution of (trans)-3-[3-(6-phenyl-1,3,5-hexatriynyl)oxiranyl]-2-propenal (50 mg, 0.20 mmole; see Example 5) in 6 ml of dry tetrahydrofuran. The mixture was stirred for 2 hours at −78° C. and was then quenched at that temperature by the dropwise addition of ca. 0.5 ml of a solution of methanol-acetic acid 4:1. The mixture was warmed to room temperature, water was added and the mixture was extracted with ether. The combined ether extracts were washed with water and saturated aqueous sodium chloride and were dried over anhydrous magnesium sulfate. Removal of solvent gave an oil which was purified by preparative thin layer chromatography (ethyl acetate-hexane 1:1) to afford 34 mg pure title compound, melting point 65°-66° C.

Analysis Calc'd. for $C_{17}H_{12}O_2$: C, 82.24; H, 4.87. Found: C, 82.23; H, 4.99.

EXAMPLE 7

(trans)-3-[3-(6-Phenyl-1,3,5-hexatriynyl)oxiranyl]-oxiranemethanol

To a stirred solution of 22 mg (0.089 mmole) of (trans)-3-[3-(6-phenyl-1,3,5-hexatriynyl)oxiranyl]-2-propen-1-ol (see Example 6) in 5 ml of dry benzene was added 2 mg of vanadyl acetylacetonate and 50 μl (0.26 mmole) of a 5.43M solution of t-butylhydroperoxide in benzene. The mixture was stirred for 4 hours. The mixture was concentrated and the residue was purified via preparative thin layer chromatography (silica gel; ethyl acetate-hexane 1:1) to afford 11 mg of the title compound as an approximately 1:1 mixture of diastereomers.

What is claimed is:

1. A compound having the formula

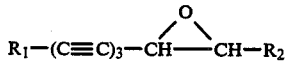

wherein $R_1$ is phenyl or phenyl substituted with 1, 2 or 3 halogen, alkyl of 1 to 4 carbons, alkoxy of 1 to 4 carbons, or trifluoromethyl groups, and $R_2$ is hydroxymethyl, carboxyaldeyde, propenalyl, 3-hydroxy-1-propenyl or 3-hydroxy-1,2-epoxypropyl.

2. A compound in accordance with claim 1 wherein $R_2$ is 3-hydroxy-1,2-epoxypropyl.

3. A compound in accordance with claim 1 wherein $R_1$ is phenyl.

4. A compound in accordance with claim 1 wherein $R_2$ is hydroxymethyl.

5. A compound in accordance with claim 1 wherein $R_2$ is carboxyaldehyde.

6. A compound in accordance with claim 1 wherein $R_2$ is propenalyl.

7. A compound in accordance with claim 1 wherein $R_2$ is 3-hydroxy-1-propenyl.

8. The compound in accordance with claim 1, (trans)-3-(6-phenyl-1,3,5-hexatriynyl)oxiranemethanol.

9. The compound in accordance with claim 1, (trans)-3-(6-phenyl-1,3,5-hexatriynyl)oxiranecarboxaldehyde.

10. The compound in accordance with claim 1, (trans)-3-[3-(6-phenyl-1,3,5-hexatriynyl)oxiranyl]-2-propenal.

11. The compound in accordance with claim 1, (trans)-3-[3-(6-phenyl-1,3,5-hexatriynyl)oxiranyl]-oxiranemethanol.

12. The compound in accordance with claim 1, (trans)-3-[3-(6-phenyl-1,3,5-hexatriynyl)oxiranyl]-2-propen-1-ol.

* * * * *